United States Patent
Wu

(10) Patent No.: US 8,449,835 B2
(45) Date of Patent: May 28, 2013

(54) DEVICE FOR FECAL OCCULT BLOOD TEST

(75) Inventor: Ming-Feng Wu, Taichung (TW)

(73) Assignee: Taichung Veterans General Hospital, Taichung (TW)

( * ) Notice: Subject to any disclaimer, the term of this patent is extended or adjusted under 35 U.S.C. 154(b) by 116 days.

(21) Appl. No.: 13/252,025

(22) Filed: Oct. 3, 2011

(65) Prior Publication Data
US 2012/0083028 A1    Apr. 5, 2012

(30) Foreign Application Priority Data
Oct. 4, 2010   (TW) ................................ 99133761 A

(51) Int. Cl.
*B01L 3/00* (2006.01)
*G01N 31/22* (2006.01)
*G01N 33/52* (2006.01)
*G01N 21/75* (2006.01)
*G01N 33/72* (2006.01)
*G01N 33/53* (2006.01)
*C12M 1/34* (2006.01)
*C12M 3/00* (2006.01)
*C12M 1/26* (2006.01)

(52) U.S. Cl.
USPC ............. 422/430; 422/405; 422/409; 436/66; 436/808; 436/810; 435/287.6; 435/309.1

(58) Field of Classification Search
USPC .......... 422/430; 436/66, 808, 810; 435/287.6, 435/309.1, 309.3
See application file for complete search history.

(56) References Cited

U.S. PATENT DOCUMENTS

| 4,409,988 A * | 10/1983 | Greenspan .................... 600/572 |
| 7,993,871 B2 * | 8/2011 | Skiffington et al. ............ 435/30 |
| 2008/0260581 A1 * | 10/2008 | Rosman et al. .............. 422/68.1 |
| 2008/0286831 A1 * | 11/2008 | Liang ............................. 435/34 |

FOREIGN PATENT DOCUMENTS

| TW | 158150 | 5/1991 |
| TW | M328287 U | 3/2008 |
| TW | M332847 U | 5/2008 |
| WO | WO 03068398 A1 * | 8/2003 |

* cited by examiner

*Primary Examiner* — Jill Warden
*Assistant Examiner* — Charles D Hammond
(74) *Attorney, Agent, or Firm* — Cheng-Ju Chiang

(57) ABSTRACT

A devise for fecal occult blood test comprises a first and a second casings, a sampling portion extending from the first casing, a specimen processing portion, at least a testing portion and a packing cylindrical member. The packing cylindrical member is coupled between the first and second casings when unused and dismantled therefrom when used. After sampling via a specimen collecting portion of the sampling portion, the specimen collecting portion is drawn into the first casing to reduce the device size. The first and second casings are fixedly coupled together in a specimen processing position thereof to mix specimens with a liquid of the specimen processing portion into a testing liquid, and then in a specimen testing position thereof to disperse onto the testing portions for testing and directly display test results. The present invention advantages high accuracy, rather hygiene, significant size reduction, real-time testing-result display and convenient use.

9 Claims, 9 Drawing Sheets

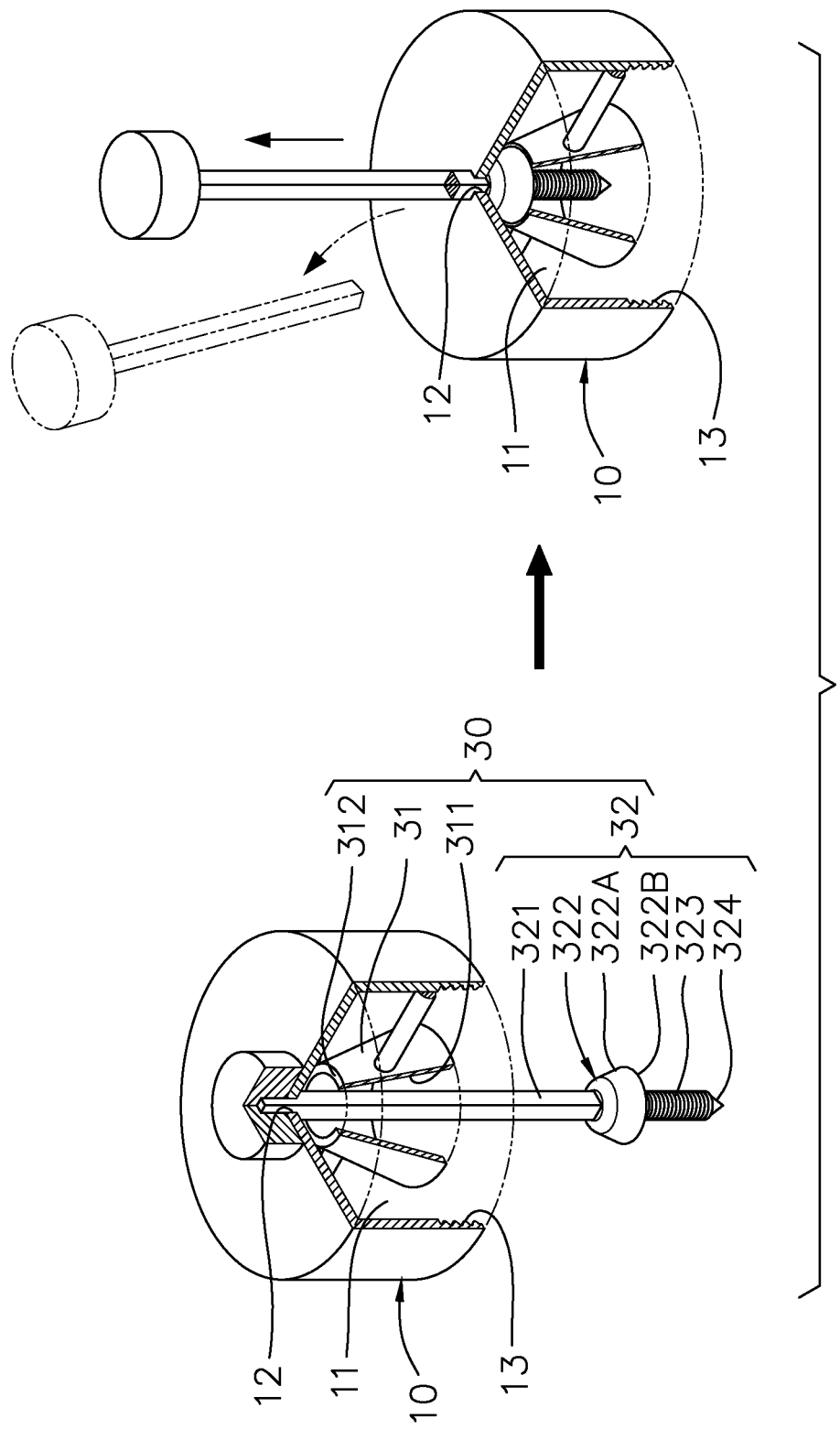

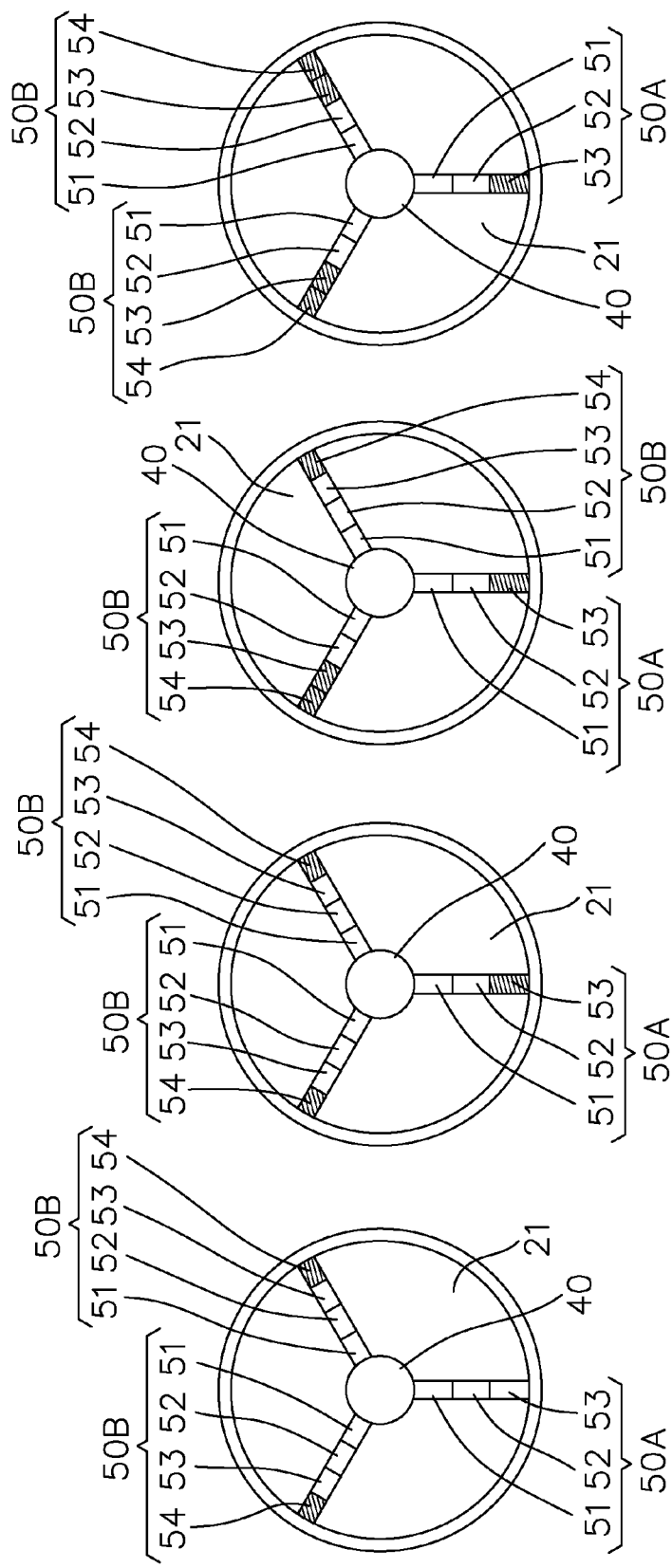

US 8,449,835 B2

DEVICE FOR FECAL OCCULT BLOOD TEST

BACKGROUND OF THE INVENTION

1. Field of the Invention

The present invention relates to a test device, and particularly to a device for fecal occult blood test having advantages of high test accuracy, well hygiene maintenance, significant size reduction, real-time test-result display and convenient use, etc.

2. Related Art

Conventional fecal test structures essentially include chemical (guaiac) test structures, immunochemical test structures, and test structures combining chemical tests and immunochemical tests. Whichever the aforementioned test structures are in use, all of them respectively have drawbacks as follows:

[1] False positive result: Conventional chemical test structures are disclosed in Taiwan Patent Nos. 158150 (Multi-Functional Excrement Testing Apparatus), M328287 (Safety Excrement Testing Device) and M332847 (Apparatus for Occult Blood Test), etc. However, for all of the above-disclosed test structures, specimens and reagents thereof have to be tested additionally after sampling. Such process is very inconvenient and results in a high percentage of false positive results.

[2] Unhygienic: Hand smearing happens very easily when sampling for the conventional chemical and immunochemical test structures. Furthermore, smell of the specimens thereof is easily sensed when the specimens and reagents are tested additionally. Such process is considered to be very unhygienic.

[3] Large size: Specimens for the conventional immunochemical test structures have to be mixed with buffer solutions additionally to become test solutions after sampling. Such process is unhygienic and is in need of large test equipment of laboratories for test as well. In other words, the test structures have disadvantages of large sizes.

[4] Inconvenience in use: In addition to inconvenience for the conventional immunochemical test structures due to the need of using laboratories for test, ready-made testing equipment such as Visualine® Dual Occult Blood FaecoCheck Test is known as 2-in-1 occult blood reactive test kits. Chromogenic agent is required to add additionally for such equipment after sampling and specimens thereof are in need of using laboratories for test. As a result, use of such equipment is inconvenient as well.

Hence it is imperative to invent an improved technique to overcome the above mentioned drawbacks and problems.

SUMMARY OF THE INVENTION

Accordingly, an object of the present invention is to provide a device for fecal occult blood test having advantages of high accuracy, rather hygiene, significant size reduction, real-time test-result display and convenient use. In particular, the present invention overcomes the drawbacks of the conventional test structures of false positive results, unhygienic use, large size and inconvenient use, etc.

To solve the above drawbacks, a device for fecal occult blood test in accordance with the present invention comprises a first casing comprising a first containing portion therein and an extraction hole; a second casing comprising a second containing portion therein and a receiving groove; a sampling portion comprising: a fixing member fixed in the first containing portion and defining a passageway corresponding to the extraction hole; a sampling apparatus comprising a drawing member, a fixing end portion, a specimen collecting portion, and a puncture end portion, the drawing member being extendable out of the extraction hole and used to draw the fixing end portion through and into the passageway for positioning the fixing end portion in the passageway after sampling, the specimen collecting portion connected with the fixing end portion for temporarily positioning sampled specimens, the puncture end portion coupled with the specimen collecting portion for puncturing; a specimen processing portion disposed in the second casing and mostly located inside the second containing portion, the specimen processing portion comprising a storing chamber, a first film, a second film and a liquid, the first and second films securely storing the liquid in the storing chamber; at least a testing portion disposed in the second containing portion and communicable with the receiving groove; and a packing cylindrical member defining a packing space therein.

In the preferred embodiment of the present invention, the first and second casings are operated in positions thereof orderly from being unused to being completely used for testing, the positions comprising: [a] a packing position where the packing cylindrical member is coupled between the first and second casings, and the sampling portion and the specimen processing portion are mostly located and extend in the packing space; [b] a using position where the packing cylindrical member is dismantled from the first and second casings, and the specimen collecting portion takes samples from the specimens; [c] a specimen processing position where the specimen processing portion mostly enters the passageway, and the puncture end portion penetrates through the first film so as to produce a testing liquid by mixing the specimens with the liquid; and [d] a specimen testing position where the second film is penetrated by the puncture end portion, the testing liquid flows into the receiving groove and the at least a testing portion tests the testing liquid to show directly test results.

BRIEF DESCRIPTION OF THE DRAWINGS

FIG. 5 is a schematic view showing a drawing member of the present invention before being drawn, after being drawn and after removing;

FIGS. 9A, 9B, 9C and 9D are schematic views showing different test results of chemical test papers and immunoassay test papers of the present invention.

DESCRIPTION OF THE PREFERRED EMBODIMENTS

Figure 1:
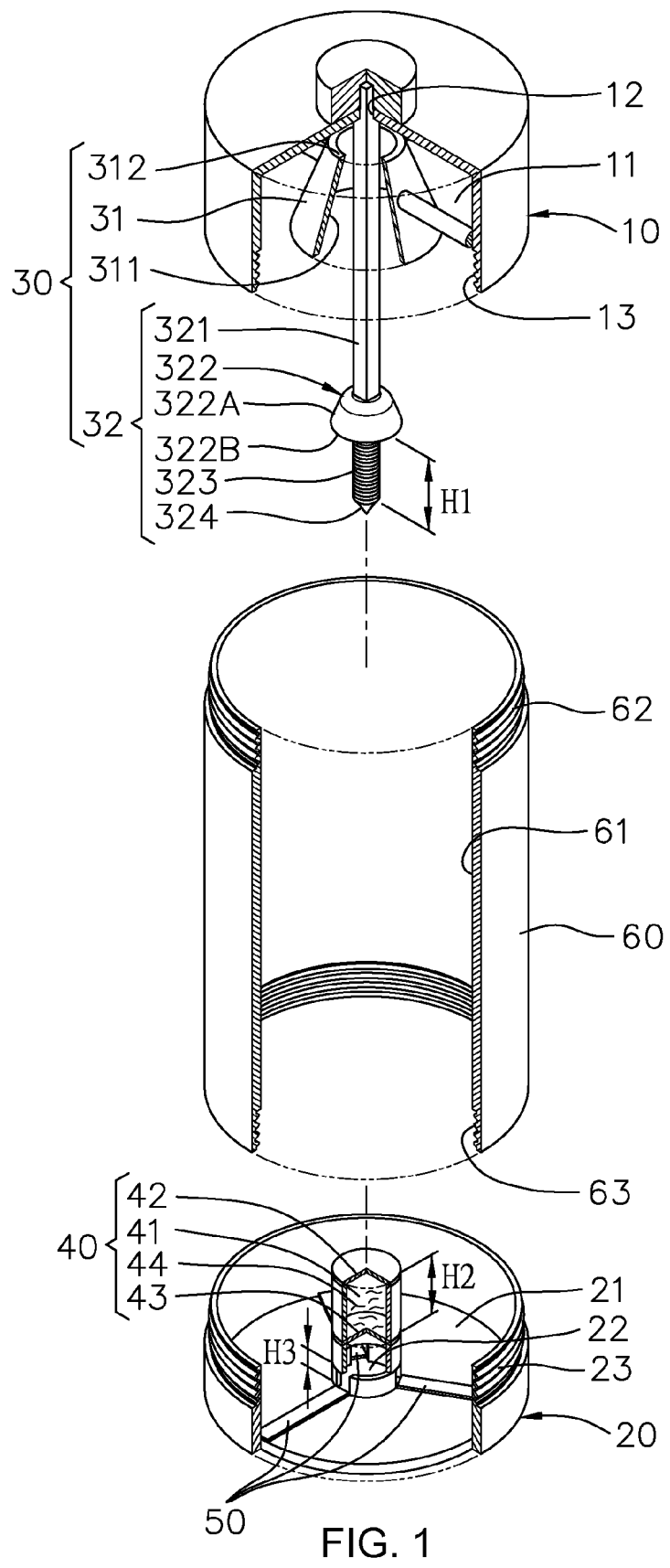
FIG. 1 is a schematic exploded view of a device for fecal occult blood test of the present invention.

It has to be mentioned in advance that colorectal cancer is currently ranked precedingly among civil cancers. Colorectal cancer can be preliminarily examined by conducting fecal occult blood test. Occult blood is the blood that is invisible to human bare eyes but can be found by tests. Generally, there is very little blood in normal feces. If the amount of blood is large enough to be found in feces by common tests, it means that somewhere of the tested digestive tracts is wrong. Due to low accuracy of current test devices, fecal occult blood still needs to be tested in medical laboratories after sampling, and therefore such test process is quite cumbersome and inconvenient.

Referring to FIGS. 1 to 4, a device for fecal occult blood test comprises a first casing 10, a second casing 20, a sampling portion 30, a specimen processing portion 40, at least one testing portion 50 and a packing cylindrical member 60. The first casing 10 comprises a first containing portion 11 therein and an extraction hole 12. The second casing 20 comprises a second containing portion 21 therein and a receiving groove 22.

The sampling portion 30 comprises a fixing member 31 fixed in the first containing portion 11 and defining a passageway 311 corresponding to the extraction hole 12, a sampling apparatus 32 having a drawing member 321, a fixing end portion 322, a specimen collecting portion 323, and a puncture end portion 324. The drawing member 321 is extendable out of the extraction hole 12 and used to draw in the fixing end portion 322 through the passageway 311 and position the fixing end portion 322 in the passageway 311 (as shown in FIG. 5). The specimen collecting portion 323 is connected with the fixing end portion 322 for temporarily positioning sampled specimens. The puncture end portion 324 is coupled with the specimen collecting portion 323 for puncturing.

Figure 2:
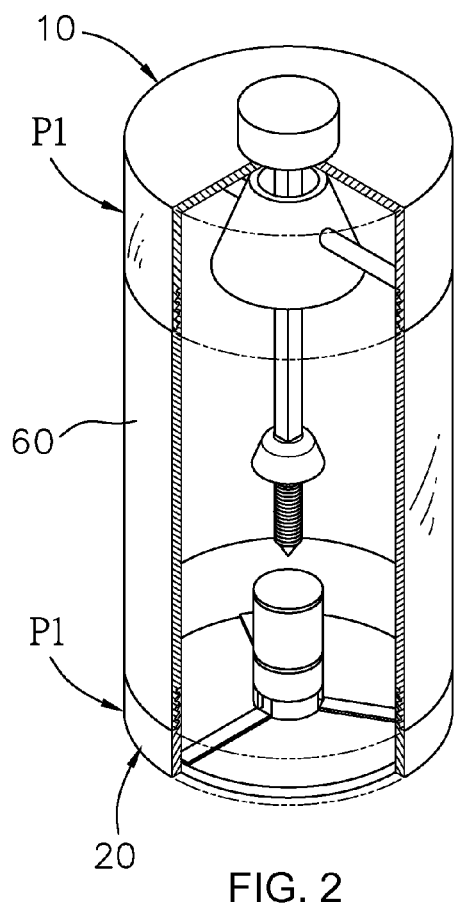
FIG. 2 is a schematic view of the device of the present invention in a packing position thereof.

The specimen processing portion 40 is disposed in the second casing 20 and mostly located inside the second containing portion 21. The specimen processing portion 40 comprises a storing chamber 41, a first film 42, a second film 43, and a liquid 44. The first and second films 42, 43 are used to securely store the liquid 44 in the storing chamber 41. At least one testing portion 50 is disposed in the second containing portion 21 and communicable with the receiving groove 22. The packing cylindrical member 60 defines a packing space 61 therein, With the above described structure, the first and second casings 10, 20 are operated in the following positions orderly from being unused to being completely used for testing:

[a] A packing position P1: Referring to FIG. 2, the packing cylindrical member 60 is coupled between the first and second casings 10, 20, and the sampling portion 30 and the specimen processing portion 40 are mostly located and extend in the packing space 61.

Figure 8A:
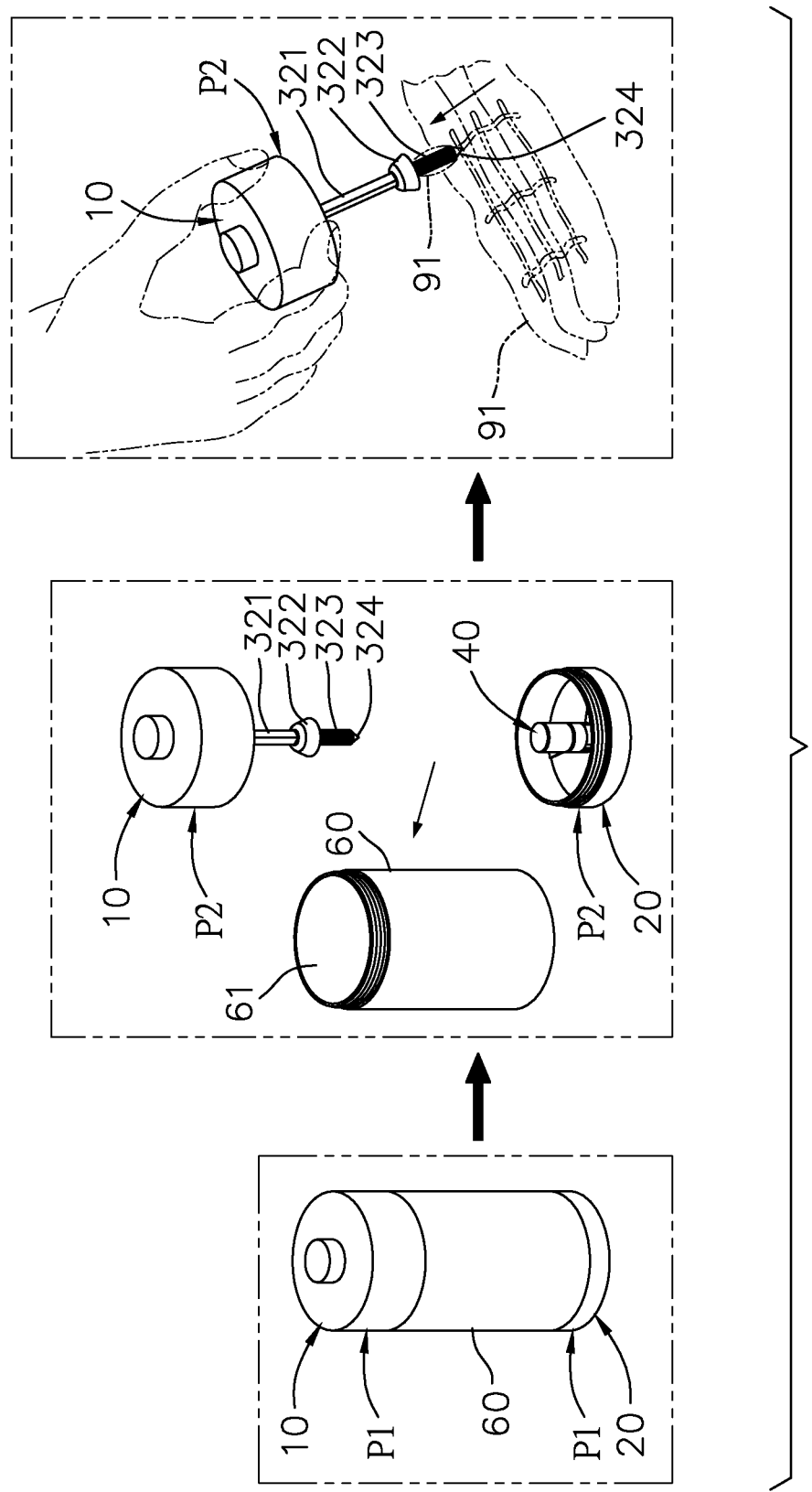
FIG. 8A is a schematic view showing a first test process of the present invention.

[b] A using position P2: Referring to FIG. 8A, the packing cylindrical member 60 is dismantled from the first and second casings 10, 20, and the specimen collecting portion 323 takes samples from the specimens 91.

Figure 3:
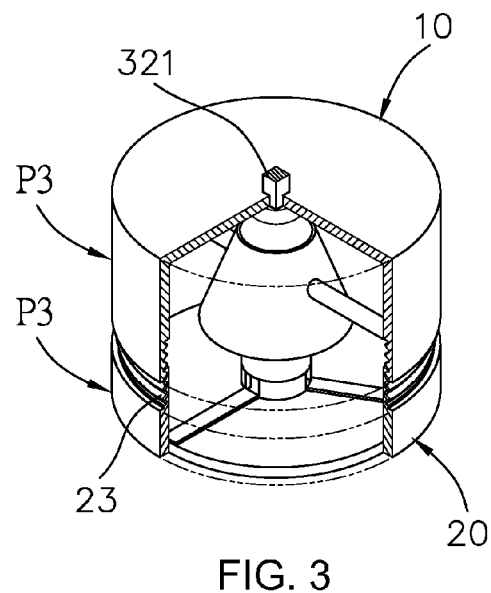
FIG. 3 is a schematic view of the device of the present invention in a specimen processing position thereof.
Figure 8B:
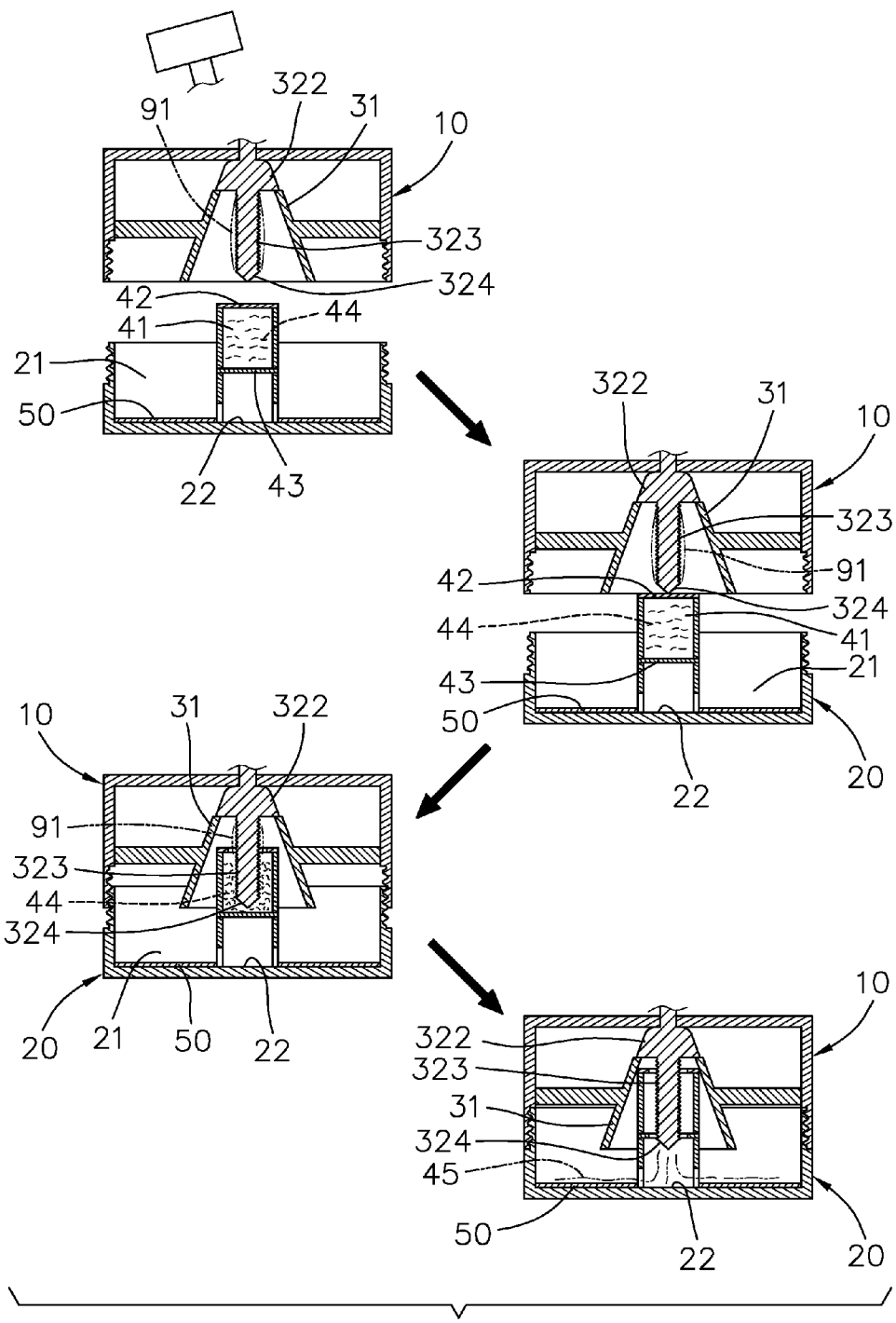
FIG. 8B is a schematic view showing a second test process of the present invention.

[c] A specimen processing position P3: Referring to FIG. 3, the specimen processing portion 40 mostly enters the passageway 311, and the puncture end portion 324 penetrates through the first film 42 so as to produce a testing liquid 45 (as shown in FIG. 8B) by mixing the specimens 91 with the liquid 44.

Figure 4:
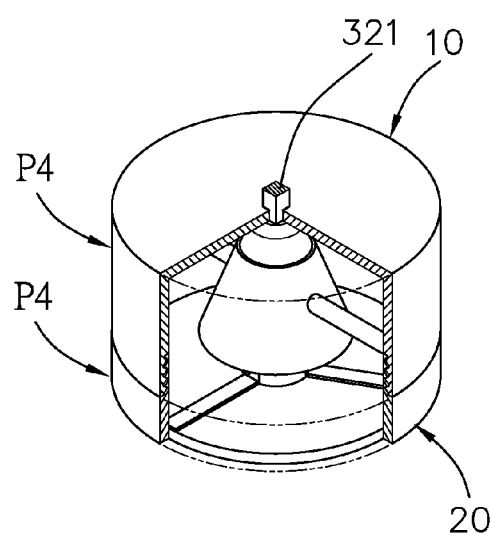
FIG. 4 is a schematic view of the device of the present invention in a specimen testing position thereof.

[d] A specimen testing position P4: Referring to FIG. 4, the second film 43 is penetrated by the puncture end portion 324, the testing liquid 45 flows into the receiving groove 22, and the at least one testing portion 50 tests the testing liquid 45 to directly show test results.

In practice, for the preferred embodiment, the second casing 20 comprises a seeing-through portion capable of showing testing results of the testing portion 50 while testing the testing liquid 45.

The first and second casings 10, 20 form a first thread portion 13 and a second thread portion 23 respectively so as to engage with each other for fixture thereof. The puncture end portion 324 is driven to sequentially penetrate the first and second films 42, 43 during engagement and fixture of the first and second casings 10, 20.

The packing cylindrical member 60 forms a first screw portion 62 and a second screw portion 63 at two opposite ends of the packing cylindrical member 60. The first screw portion 62 is used to engage and fix with the first thread portion 13, and the second screw portion 63 is used to engage and fix with the second thread portion 23.

Figure 6:
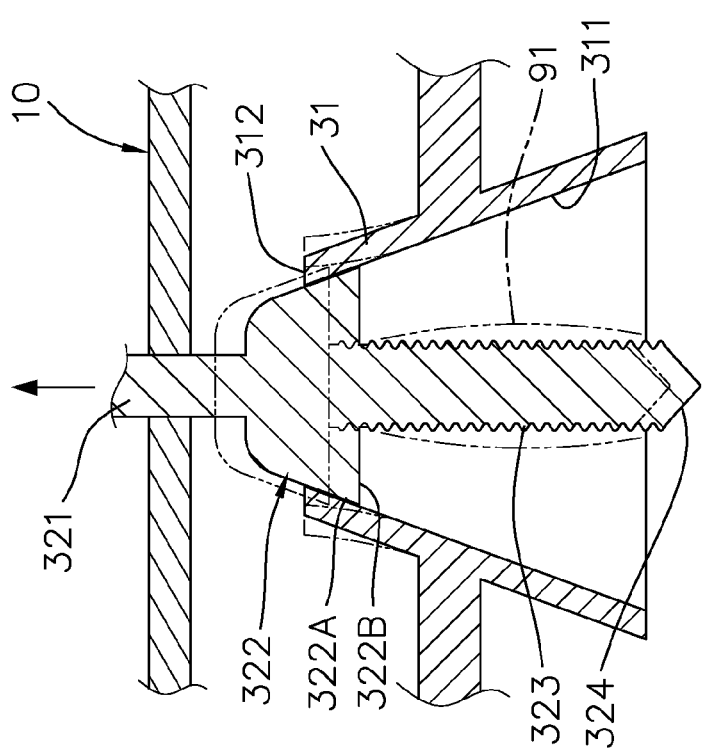
FIG. 6 is a schematic view showing a fixing end portion of the present invention not yet fixed in a passageway of the present invention.

The passageway 311 is gradually narrowed in width from a bottom of the passageway 311 to a top thereof. The passageway 311 further forms a restriction top rim 312 (as shown in FIG. 6).

Figure 7:
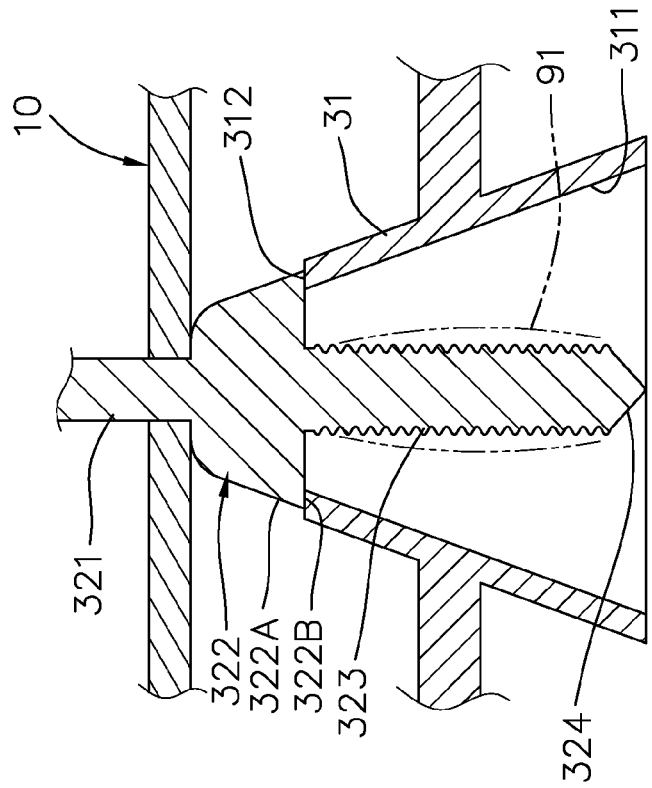
FIG. 7 is a schematic view showing the fixing end portion fixed in the passageway of the present invention.

The fixing end portion 322 comprises an outer oblique face 322A corresponding to the gradually narrowed passageway 311, and a limiting bottom face 322B corresponding to the restriction top rim 312. After sampling, the fixing end portion 322 is drawn by the drawing member 321 (as shown in FIG. 5) until the outer oblique face 322A is forced to squeeze through the restriction top rim 312 and the limiting bottom face 322B is engaged and fixed onto the restriction top rim 312 (as shown in FIG. 7).

The specimen collecting portion 323 has a first height H1. A second height H2 is defined between the first and second films 42, 43 of the storing chamber 41. The receiving groove 22 has a third height H3. The first height H1 is larger than the second height H2 while the second height H2 is larger than the third height H3.

The liquid 44 is one of buffer solutions and physiological equal-tension solutions.

The at least one testing portion 50 can be plural, i.e., more than one (In this preferred embodiment, the number of the testing portions 50 is three). The plural testing portions 50 are radially disposed outwards from the center of the second containing portion 21. Each of the testing portions 50 can be one of chemical test papers 50A and immunoassay test papers 50B. Each of the test papers 50A, 50B (as shown of FIG. 8C) comprises a receiving part 51 (for receiving and delivering the testing liquid 45), a mixing part 52 (for mixing the testing liquid 45 with reagents), and a reacting part 53 (for testing results from reagent reaction). The receiving, mixing, and reacting parts 51, 52, 53 are arranged outwards in sequence from the center of the second containing portion 21.

For the chemical test papers 50A, the mixing part 52 can be any organic peroxide or indicator cooperating with the reacting part 53.

For the immunoassay test papers 50B, the mixing part 52 can be a compound with color colloid accompanying with anti-human-hemoglobin antibody, and the reacting portion 53 can be a secondary antibody. Furthermore, a confirmation part 54 is disposed next to the reacting part 53 for confirming the testing liquid 45 certainly and completely flows through the testing portion 50 in order to improve test accuracy (for example, the confirmation part 54 can be a test paper attached with a heterophile (non-specific) antibody or other kinds of test papers having contents capable of reacting with the flowing-through liquid).

It is particularly noted that for a chemical test, pseudoperoxidase of the hemoglobin of red blood cells are commonly utilized to catalyze guaiac and hydrogen peroxide ($H_2O_2$) to generate a blue reaction (positive reaction). Since animal blood, muscle, internal organs, medicine and some kinds of vegetables and fruits contain peroxidase, they may cause false positive reactions on a chemical test paper.

For an immunochemical test, an antiserum or antibody reacting to human hemoglobin is utilized to perform antigen-antibody reaction. Such reaction is not affected by food peroxidase, animal blood and vitamin C and has higher test sensitivity so as to be appropriate for tests on low-concentration occult blood in feces. The main reason that the immunochemical test is appropriate for qualitative test paper analysis is that the test paper thereof is embedded with compounds having color colloid accompanying anti-human-hemoglobin antibody (i.e. the mixing part 52). When specimens contain human hemoglobin, the human hemoglobin will combine with the compounds, and then move by absorption to the secondary antibody (i.e. the reacting part 53) and combine therewith so as to present a color band (i.e. positive reaction). Additional compounds having color colloid accompanying anti-human-hemoglobin antibody continue moving to test papers containing the non-specific antibody (i.e. the confirmation part 54) so as to combine therewith and present another color band.

Processes of using the device of the present invention are described as follows. Firstly, referring to FIG. 8A, before using the device of the present invention, the packing cylindrical member 60 is coupled between the first and second casings 10, 20 (both of them in the packing position P1) for protecting the sampling portion 30 and the specimen processing portion 40. When in use, the packing cylindrical member 60 is dismantled from the first and second casings 10, 20 (both of them in the position P2), and the first casing 10 is held towards the specimen 91 for sampling via the sampling apparatus 32 (generally, the sampling apparatus 32 takes samples from the feces via scratching several lines on the feces along both of longitudinal and transversal directions thereof). Afterwards, the specimen collecting portion 323 is drawn via the drawing member 321 so as to be mostly positioned in the passageway 311 and therefore disengage the drawing member 321 from the fixing end portion 322 (as shown in FIGS. 5 and 8B, a small stub of the drawing member 321 may be left, but a size of the undesired structure is significantly reduced).

Figure 8C:
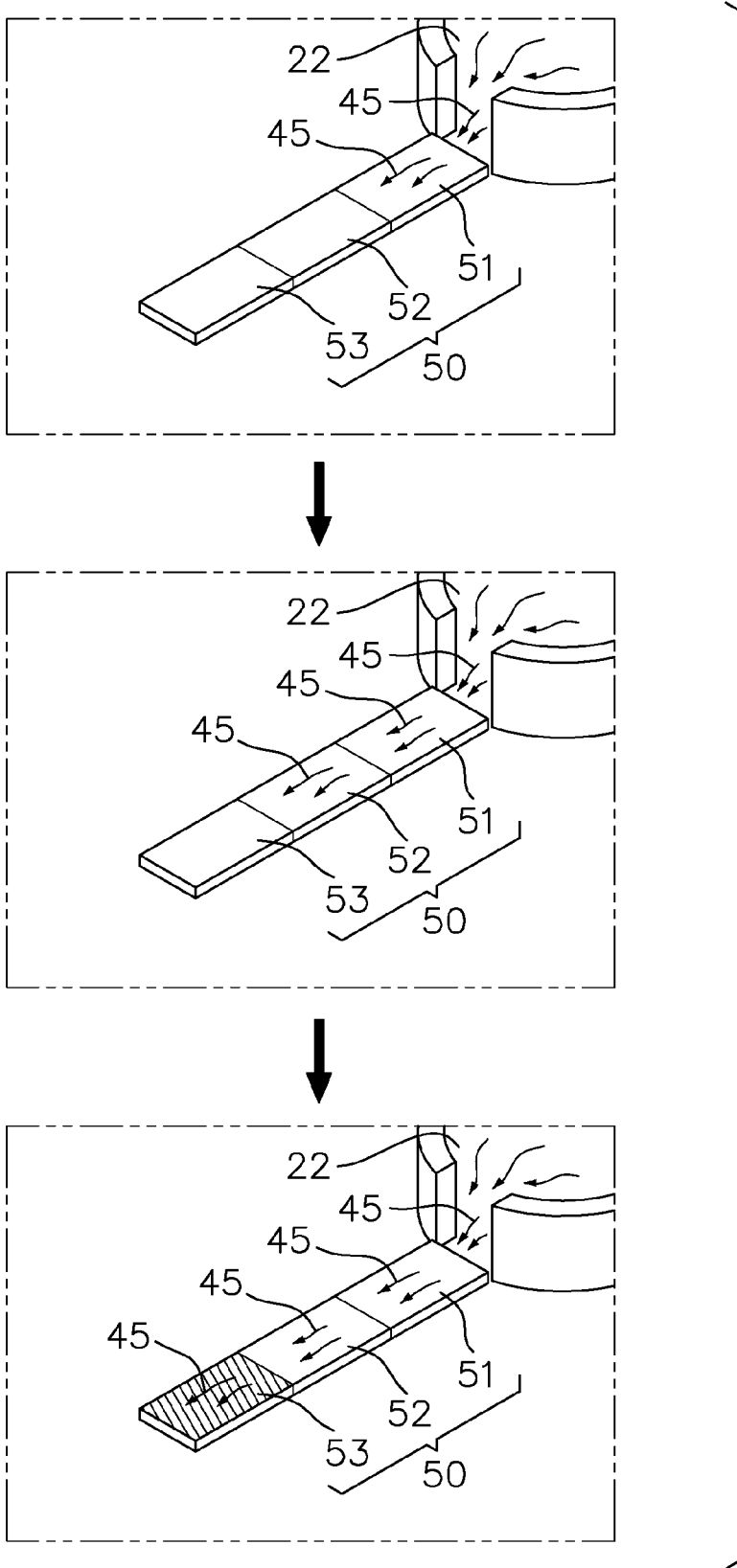
FIG. 8C is a schematic view showing a third test process of the present invention.

Next, the first and second casings 10, 20 are fixedly screwed to be in the specimen processing position P3 so as to allow the puncture end portion 324 penetrating through the first film 42. After evenly mixing the specimen 91 with the liquid 44 of the storing chamber 41 (accuracy of quantity tests can be improved), the first and second casings 10, 20 are further screwed tightly to be in the specimen testing position P4 so as to allow the puncture end portion 324 penetrating through the second film 43. The testing liquid 45 from the combined specimens 91 and liquid 44 flows into the receiving groove 22, and then disperses toward the chemical test papers 50A (as shown in FIG. 9A, for proceeding chemical fecal occult blood test) and toward the immunoassay test papers 50B (for proceeding immunochemical fecal occult blood test). Finally, the reacting part 53 directly presets testing results (as shown in FIG. 8C).

Further in detail, if animal internal organs or muscle has been eaten, the feces are likely to generate false positive test reaction similar to occult blood. Accordingly, the device of the present invention is simultaneously equipped with both the chemical test papers 50A and the immunoassay test papers 50B (as shown in FIG. 9A, the immunoassay test papers 50B are further categorized into low-concentration test papers and high-concentration test papers). In the event that there is no reaction to both of the chemical and immunoassay test papers, digestive tracts of the tested essentially have almost no occult blood problem. Otherwise, in the event that only the chemical test papers 50A indicate positive reaction (as shown in FIG. 9B), the upper digestive tracts of the tested are likely to bleed or just chemical reaction due to eating animal organs (false positive). However, if even the reagents of the low-concentration occult blood test papers have reactions (as shown in FIG. 9C, the reagents of the low-concentration test papers show reactions), the digestive tracts of the tested are likely to be slightly pathological. If even the reagents of the high-concentration occult blood test papers have reactions (as shown in FIG. 9D), the tested is advised to quickly go to the hospitals for detailed physical examination.

Figure 9G:
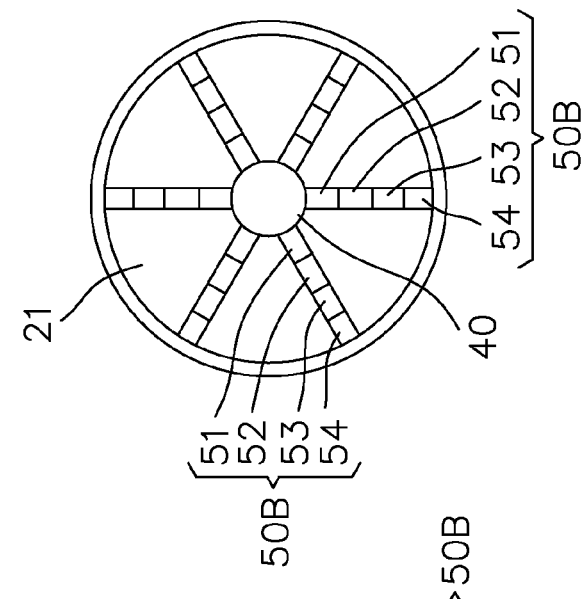
FIGS. 9E, 9F and 9G are schematic views showing various embodiments of the testing portions in accordance with the present invention.
Figure 9F:
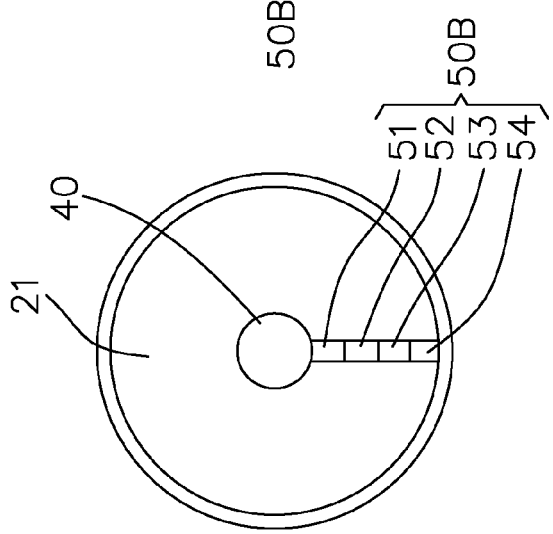
Figure 9E:
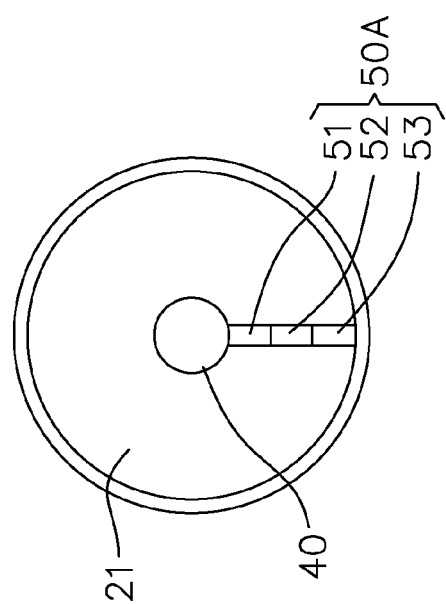

Certainly, depending on practical requirements, the testing portion 50 can be designed and exemplified to be single chemical test papers 50A (as shown in FIG. 9E), single immunoassay test papers 50B (as shown in FIG. 9F), or a plurality of the immunoassay test papers 50B (as shown in FIG. 9G, for enhancing test accuracy).

Accordingly, the present invention has advantages and effects as follows:

[1] High accuracy: The specimen 91 of the present invention is well mixed with the liquid 44 into the testing liquid 45 before being tested by the testing portion 50. This way enhances accuracy of qualitative and quantitative occult blood screening and monitoring results.

[2] Relatively hygienic: The sampling apparatus 32 of the present invention is drawn by the drawing member 321 to be positioned in the passageway 311 after sampling onto the specimens 91. No hand touch on the specimen 91 is necessary from the process of taking samples to the process of samples being received between the first and second casings 10, 20, and therefore the entire process is rather hygienic.

[3] Significantly reduced size: The drawing member 321 is capable to be removed after the sampling apparatus 32 is drawn into the passageway 311 when sampling completes, and thus the size of the device is greatly reduced. Size reduction of the device benefits transportation of the device if the test results of the device need to forward to medical organizations for further interpretation of the testing results.

[4] Real-time display of test results: Test results are displayed immediately after test papers 50A, 50B of the present invention are mixed with the testing liquid 45, and hence no complicated test instruments are required for operation convenience.

[5] Convenience in use: The using process of the device of the present invention includes the serial steps of separating casings 10, 20, sampling, mixture, testing, and presenting testing results, etc., and is simple to operate. Such using process can be easy and convenient to perform in a hospital, retirement center, or organization without standard laboratories, or for personal use.

While the present invention is demonstrated herein with reference to the preferred embodiments, it is to be understood that the foregoing embodiments may be slightly modified or changed without departing from the spirit and scope of the present invention.

What is claimed is:

1. A device for fecal occult blood test, comprising:
   a first casing comprising a first containing portion therein and an extraction hole;
   a second casing comprising a second containing portion therein and a receiving groove;
   a sampling portion comprising:
      a fixing member fixed in the first containing portion and defining a passageway corresponding to the extraction hole; and
      a sampling apparatus comprising a drawing member, a fixing end portion, a specimen collecting portion, and a puncture end portion, the drawing member being extendable out of the extraction hole and used to draw the fixing end portion through and into the passageway for positioning the fixing end portion in the passageway after sampling, the specimen collecting portion connected with the fixing end portion for temporarily positioning sampled specimens, the puncture end portion coupled with the specimen collecting portion for puncturing;
   a specimen processing portion disposed in the second casing and mostly located inside the second containing portion, the specimen processing portion comprising a storing chamber, a first film, a second film and a liquid, the first and second films securely storing the liquid in the storing chamber;
   at least a testing portion disposed in the second containing portion and communicable with the receiving groove; and
   a packing cylindrical member defining a packing space therein;
   wherein the first and second casings are operated in positions thereof orderly from being unused to being completely used for testing, the positions comprising:
      [a] a packing position where the packing cylindrical member is coupled between the first and second casings, and the sampling portion and the specimen processing portion are mostly located and extend in the packing space;
      [b] a using position where the packing cylindrical member is dismantled from the first and second casings, and the specimen collecting portion takes samples from the specimens;
      [c] a specimen processing position where the specimen processing portion mostly enters the passageway, and the puncture end portion penetrates through the first film so as to produce a testing liquid by mixing the specimens with the liquid; and
      [d] a specimen testing position where the second film is penetrated by the puncture end portion, the testing liquid flows into the receiving groove and the at least a testing portion tests the testing liquid to show directly test results.

2. The device for fecal occult blood test of claim 1, wherein the second casing comprises a see-through portion capable of directly displaying the testing results of the testing portion while testing the testing liquid.

3. The device for fecal occult blood test of claim 1, wherein the first and second casings form a first thread portion and a second thread portion respectively so as to engage with each other for fixture thereof, the puncture end portion is driven to sequentially penetrate the first and second films during engagement and fixture of the first and second casings.

4. The device for fecal occult blood test of claim 3, wherein the packing cylindrical member forms a first screw portion and a second screw portion at two opposite ends of the packing cylindrical member, the first screw portion is used to engage and fix with the first thread portion, and the second screw portion is used to engage and fix with the second thread portion.

5. The device for fecal occult blood test of claim 1, wherein the passageway is gradually narrowed in width from a bottom of the passageway to a top thereof, and further forms a restriction top rim, the fixing end portion comprises an outer oblique face corresponding to the gradually narrowed passageway, and a limiting bottom face corresponding to the restriction top rim, wherein after sampling, the fixing end portion is drawn by the drawing member until the outer oblique face is forced to squeeze through the restriction top rim, and the limiting bottom face is engaged and fixed onto the restriction top rim.

6. The device for fecal occult blood test of claim 1, wherein the liquid is one of buffer solutions and physiological equal-tension solutions.

7. The device for fecal occult blood test of claim 1, wherein a number of the at least a testing portion is more than one, and the at least a testing portion is radially disposed outwards from a center of the second containing portion, the at least a testing portion is at least one of chemical test papers and immunoassay test papers.

8. The device for fecal occult blood test of claim 7, wherein each of the chemical test papers comprises a receiving part, a mixing part and a reacting part, the receiving, mixing and reacting parts are arranged outwards in sequence from the center of the second containing portion.

9. The device for fecal occult blood test of claim 7, wherein each of the immunoassay test papers comprises a receiving part, a mixing part, a reacting part and a confirmation part, the receiving, mixing, reacting and confirmation parts are arranged outwards in sequence from the center of the second containing portion.

* * * * *